US009429536B2

(12) United States Patent
BelBruno et al.

(10) Patent No.: US 9,429,536 B2
(45) Date of Patent: Aug. 30, 2016

(54) AIRBORNE CONTAMINANT SENSOR DEVICE AND METHOD FOR USING THE SAME

(75) Inventors: Joseph J. BelBruno, Hanover, NH (US); Susanne E. Tanski, Grantham, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 13/495,258

(22) Filed: Jun. 13, 2012

(65) Prior Publication Data

US 2013/0040399 A1     Feb. 14, 2013

Related U.S. Application Data

(63) Continuation-in-part of application No. PCT/US2011/051169, filed on Sep. 12, 2011.

(60) Provisional application No. 61/466,101, filed on Mar. 22, 2011, provisional application No. 61/381,512, filed on Sep. 10, 2010.

(51) Int. Cl.
*G01N 27/12* (2006.01)
*G01N 33/00* (2006.01)

(52) U.S. Cl.
CPC .......... *G01N 27/126* (2013.01); *G01N 33/0073* (2013.01)

(58) Field of Classification Search
CPC ... G01N 33/5438; G01N 27/403; G01N 7/04; G01N 27/12; G01N 1/2214; G01N 1/24; G01N 30/00; G01N 21/783; G01N 27/126; G01N 2030/025; G01N 1/2226; G01N 31/12; B01J 19/0046; B01J 2219/00527; B01J 2219/00585
USPC ........................................ 436/149; 422/88, 83
See application file for complete search history.

(56) References Cited

U.S. PATENT DOCUMENTS

| | | | | | |
|---|---|---|---|---|---|
| 5,208,301 | A | * | 5/1993 | Epstein .............. | C08G 73/0266 525/534 |
| 5,244,562 | A | * | 9/1993 | Russell .............. | A61B 5/14532 204/403.06 |
| 5,252,292 | A | * | 10/1993 | Hirata et al. ..................... | 422/98 |
| 5,536,473 | A | * | 7/1996 | Monkman et al. ............... | 422/90 |

(Continued)

FOREIGN PATENT DOCUMENTS

| | | |
|---|---|---|
| KR | 100977292 B1 | 8/2010 |
| WO | WO 2008/007359 A2 | 1/2008 |

(Continued)

OTHER PUBLICATIONS

Highly Sensitive Detection and Discrimination of Biogenic Amines Utilizing Arrays of Polyaniline/Carbon Black Composite Vapor Detectors Gregory A. Sotzing, Jennifer N. Phend, Robert H. Grubbs, and Nathan S. Lewis Chem. Mater. 2000, 12, 593-595.*

(Continued)

*Primary Examiner* — Krishnan S Menon
*Assistant Examiner* — Dwan A Gerido
(74) *Attorney, Agent, or Firm* — Lathrop & Gage LLP (57) ABSTRACT

The present invention is a nanotechnology-based personal sensor device composed of molecularly imprinted polymers that are interrogated using radio frequency identification (RFID) technology for use in simultaneously monitoring airborne contaminants, e.g., of second-hand cigarette smoke.

17 Claims, 6 Drawing Sheets

(56) References Cited

U.S. PATENT DOCUMENTS

| | | | |
|---|---|---|---|
| 6,807,842 | B2 | 10/2004 | Williams et al. |
| 2003/0004426 | A1* | 1/2003 | Melker et al. ............... 600/532 |
| 2004/0126814 | A1 | 7/2004 | Singh et al. ................. 435/7.1 |
| 2005/0126909 | A1* | 6/2005 | Weiller et al. ............... 204/418 |
| 2006/0079648 | A1 | 4/2006 | Lutsen et al. |
| 2007/0087564 | A1 | 4/2007 | Speakman ................... 438/674 |
| 2008/0093226 | A1* | 4/2008 | Briman et al. ............... 205/775 |
| 2009/0115605 | A1 | 5/2009 | Ravenis et al. .............. 340/540 |
| 2010/0039124 | A1 | 2/2010 | Belbruno et al. ............ 324/693 |
| 2010/0193376 | A1 | 8/2010 | Rius Ferrus et al. |

FOREIGN PATENT DOCUMENTS

| | | |
|---|---|---|
| WO | WO 2008/063204 A2 | 5/2008 |
| WO | 2011136548 A3 | 11/2011 |

OTHER PUBLICATIONS

Sambe et al. "Uniformly-sized, Molecularly Imprinted Polymers for Nicotine by Precipitation Polymerization" Journal of Chromatography A 2006 1134:89-94.

Thoelen et al. "A MIP-based Impedimetric Sensor for the Detection of Low-MW Molecules" Biosensors and Bioelectronics 2008 23:913-918.

International Search Report from PCT/US2011/51169, Jan. 30, 2012, PCT.

Belbruno, et al., Sensor and Actuators B vol. 155(2), pp. 915-918, Feb. 2, 2011.

International Search Report issued in PCT/US2012/053119 dated Feb. 27, 2013, 3 pages.

\* cited by examiner

AIRBORNE CONTAMINANT SENSOR DEVICE AND METHOD FOR USING THE SAME

This patent application is a continuation-in-part application of PCT/US2011/051169, filed Sep. 12, 2011, which claims the benefit of priority from U.S. Provisional Application Ser. No. 61/466,101 filed Mar. 22, 2011 and from U.S. Provisional Application Ser. No. 61/381,512 filed Sep. 10, 2010, the content of each of which is herein incorporated by reference in its entirety.

BACKGROUND OF THE INVENTION

Molecular imprinting is a technique that allows for the production of molecule specific receptors that are analogous to biological receptor binding sites without the cost or environmental sensitivity of the natural systems (Shea (1994) *Trends Polym. Sci.* 2:166; Wulff (1995) *Angew. Chem. Int. Ed.* 34:1812; Mosbach & Ramstrom (1996) *Biotechnology* 14:163; BelBruno (2009) *Micro and Nanosystems* 1:163). Molecularly imprinted polymers (MIPs) may be based on either covalent or non-covalent binding between the host polymer and the target or template molecule. Various MIP-based devices have been suggested for use in the detection of surface-binding molecules, inorganic compounds, organic compounds, polymers, biological molecules, nanoparticles, viruses, and biological arrays (WO 2008/063204 and US 2009/0115605).

Nicotine is a characteristic component of tobacco smoke and cotinine is a major metabolite of nicotine that is detected in the urine of smokers. Other reports of nicotine MIPs have appeared in the literature. For example, nicotine-targeted MIPs based on the synthesis of the polymer from methacrylic acid monomers have been reported (Sambe, et al. (2006) *J. Chromatog. A* 1134:88; Thoelen et al. (2008) *Biosensors and Bioelectronics* 23:913-918). However, poly (methylacrylic acid) exhibits solvent incompatibility with nicotine, thereby making the production of thin films challenging.

SUMMARY OF THE INVENTION

The present invention is a device for monitoring exposure to airborne contaminants. In one embodiment, the device is composed of at least two poly(4-vinylphenol) or nylon films, each molecular imprinted with an airborne contaminant; a sensor for detecting binding between the airborne contaminant and the film, and a radio frequency interrogator unit to read the sensor and transmit an interrogation signal. In other embodiments, the sensor is a capacitive or conductive sensor, e.g. composed of polyaniline or polycarbozole. In particular embodiments, the poly(4-vinylphenol) or nylon film is produced by phase inversion-spin coating. In another embodiment, the device is composed of a polyaniline conductive sensor, molecular imprinted with an airborne contaminant, and a radio frequency interrogator unit. In certain embodiments, the airborne contaminant is selected from the group of CO, nicotine, 4-(methylnitrosamino)-1-(3-pyridyl)-1-butanone and formaldehyde. Methods for monitoring exposure to airborne contaminants using a device of the invention is also provided.

DETAILED DESCRIPTION OF THE INVENTION

The present invention is a MIP-based personal sensor that can be readily interrogated using radio frequency identification (RFID) technology for use in simultaneously monitoring airborne contaminants, such as those from second-hand tobacco smoke. The personal monitoring device is similar to the small badges used to monitor radiation doses and can be monitored locally such that immediate feedback on exposure is provided. The specific airborne molecules detectable with the instant device include, but are not limited to, CO, nicotine, 4-(methylnitrosamino)-1-(3-pyridyl)-1-butanone (NNK) and formaldehyde. Quantification of one or a combination of these components of second-hand smoke can indicate that second-hand smoke is present.

In some embodiments, the device is composed of at least two poly(4-vinylphenol) (PVP) and/or nylon films, each molecular imprinted with an airborne contaminant; a sensor; and a radio frequency identification component. As is conventional in the art, molecular imprinting is a process by which guest or host molecules (functional monomers or polymers) are allowed to self-assemble around a molecular template, thereby forming a recognition element, which has binding sites corresponding to functional groups in the template molecule. The recognition elements form a binding cavity which is cross-linked into a matrix. The template molecule is removed, leaving behind a molecularly-imprinted polymer (MIP) complementary in shape and functionality to the template molecule, which will rebind chemical targets identical to the original molecular template. In this invention, the host molecule is PVP or nylon composite, which non-covalently binds the template molecules, has solvent compatibility with the template molecules and is capable of forming a binding cavity around airborne contaminants. For use in this invention, the nylon can be any nylon conventionally used in preparing molecular imprinted films and includes, but is not limited to, nylon 6 and nylon 6/6.

Thin films of the invention can be produced by any conventional method. However, the ability to control the thickness and formulate the films in an environment typical of printed circuit production is an important feature of film production for the instant sensors. Thus, in particular embodiments, the instant films are produced by phase inversion-spin coating onto a suitable substrate. The wet phase inversion procedure (Wang, et al. (1997) *Langmuir* 13:5396; Shibata, et al. (1999) *J. Appl. Poly. Sci.* 75:1546; Trotta, et al. (2002) *J. Membr. Sci.* 201:77) for preparation of MIPs involves a polymerized starting material that is dissolved with the template in a theta solvent. A template-host network is allowed to form in solution and precipitated by immersion in a non-solvent. Originally developed to produce MIP membranes, this procedure has been adapted to the production of thin, 300 nm to 5 µm, films via spin coating (Crabb, et al. (2002) *J. Appl. Polym. Sci.* 86:3611; Richter, et al. (2006) *J. Appl. Polym. Sci.* 101:2919; Campbell, et al. (2009) *Surface and Interface Analysis* 41:347) and hydrogen bond interactions between the template and host polymer.

By way of illustration, thin films containing PVP can be produced by mixing PVP (e.g., 10%-15% by weight) in conventional casting solution with the template molecule (e.g., about 5%-10% by weight) in a suitable solvent. For example, nicotine is readily dissolved in methanol, whereas dimethylformamide (DMF) is a suitable solvent for formaldehyde and NNK. The solution is allowed to mix at room temperature, e.g., from six to 24 hours, to form the hydrogen-bonded network in solution. Subsequently, thin films are cast onto a substrate using a spin coater at 5000-7000 rpms for about 30 seconds. The thin film is allowed to dry and the template molecule is removed by washing with water. In accordance with this invention, a separate molecular imprinted film is produced for each template molecule so that detection in the assembled device occurs independently for each airborne contaminant. In this respect, certain embodiments of the device feature at least two films each independently molecular imprinted with CO, nicotine, 4-(methylnitrosamino)-1-(3-pyridyl)-1-butanone (NNK) or formaldehyde.

The substrate of the molecular imprinted film can be a rigid or flexible material, which may be conducting, semiconducting or dielectric. The substrate can be a monolithic structure, or a multilayer or other composite structure having constituents of different properties and compositions. Suitable substrate materials include quartz, glass, alumina, mica, silicon, III-V semiconductor compounds, and other suitable materials. Optionally, additional electronic elements may be integrated into the substrate for various purposes, such as thermistors, integrated circuit elements or other elements.

To detect an interaction (i.e., binding) between a molecular imprinted film and a template molecule (i.e., airborne contaminant), the device further includes one or more sensors. Any suitable electrical property may provide the basis for sensor sensitivity, for example, electrical resistance, electrical conductance, current, voltage, capacitance, transistor on current, transistor off current, and/or transistor threshold voltage. In the alternative, or in addition, sensitivity may be based on a measurements including a combination of properties, relationships between different properties, or the variation of one or more properties over time. In some embodiments of this invention, the sensor is a capacitive sensor, a conductive sensor or a combination thereof. Depending on the type of sensor, the sensor can be a separate element of the device or integrated with the molecular imprinted film.

Capacitive sensors are well-known in the art and any suitable sensor can be employed. For example, the capacitive sensor can have a sandwich-type electrode configuration, wherein the molecular imprinted film is placed between two capacitor elements or electrodes. The electrode material can be chosen from any suitable conductor or semiconductor e.g., gold, platinum, silver, and the like. By way of illustration, the instant device can use a set of interdigitated electrodes with the molecular imprinted film coated onto the electrode assembly. Specifically, a sandwich-type capacitive sensor can be produced by depositing chromium on a glass, silicon or mica substrate by thermal evaporation. The chromium is patterned by photolithography and treated, subsequently, by wet etching. An insulating $SiO_2$ layer with a thickness between 40 nm and 200 nm is deposited onto the bottom electrode surface using an electron-gun thermal deposition technique. Subsequently, the molecular imprinted polymer layer is spun coated on the substrate surface. In the final step, a Cr film with a thickness of 70 nm is deposited on the molecular imprinted polymer film surface by thermal evaporation, followed with patterning by photolithography and wet etching.

As indicated, this device can alternatively incorporate one or more conductive sensors. In this embodiment, a conductive polymer can be used such that the template molecule becomes the doping agent. Accordingly, in the presence and absence of the template molecule, the conductivity of the polymer will be different. Conductive polymers of use in this embodiment of the invention are so-called $\pi$ electron-conjugated conductive polymers. For example, polyaniline or a derivative thereof, polypyrrole or a derivative thereof, polythiophene or a derivative thereof, or a copolymer of two or more kinds of these materials are suitable conductive polymers. By way of illustration, polyaniline films were prepared for the detection of formaldehyde (see Example 3) and nicotine (see Example 4). Accordingly, in particular embodiments, airborne contaminants are detected using a conductive polymer such as polyaniline or polycarbozole.

Figure 1:
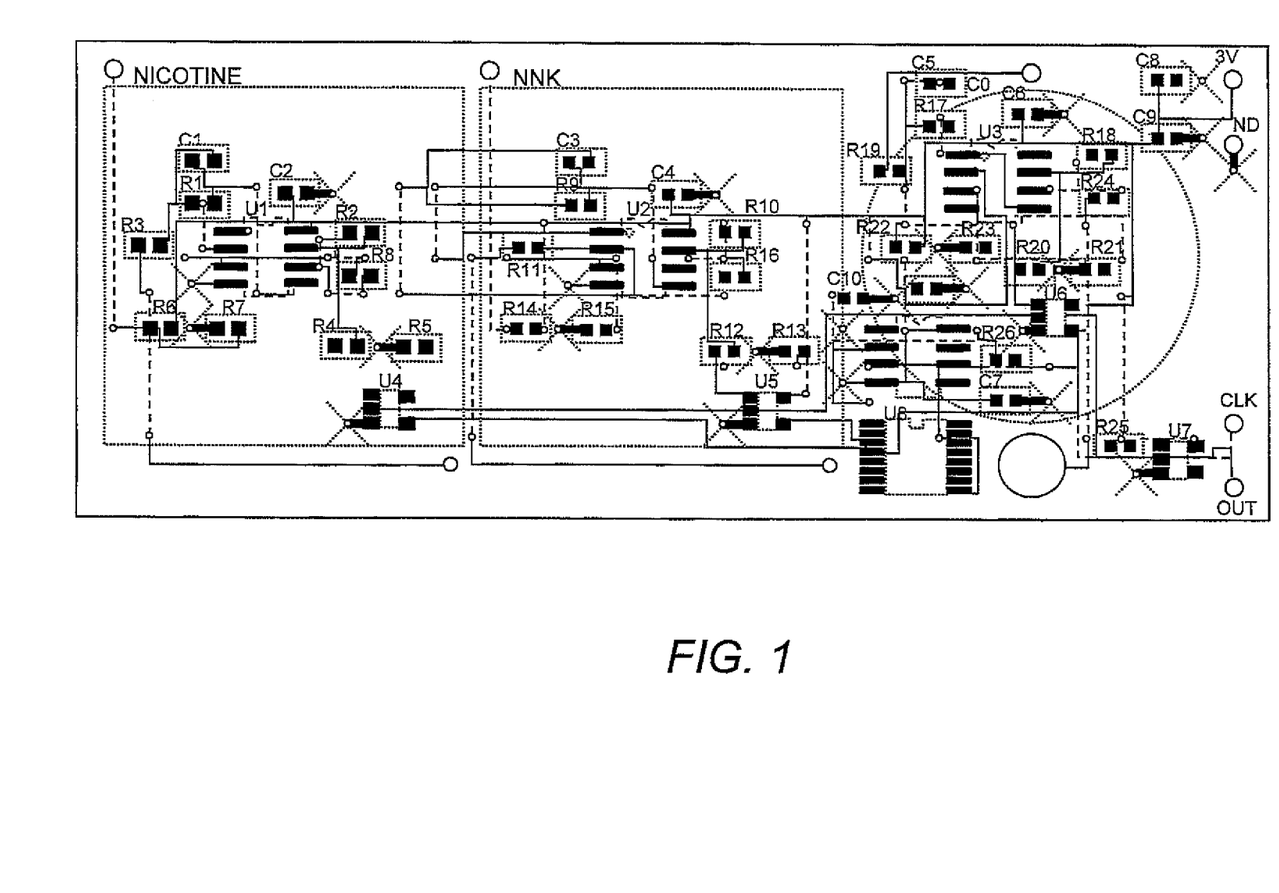
FIG. 1 is a schematic drawing of an RFID circuit of the instant device.
Figure 2A:
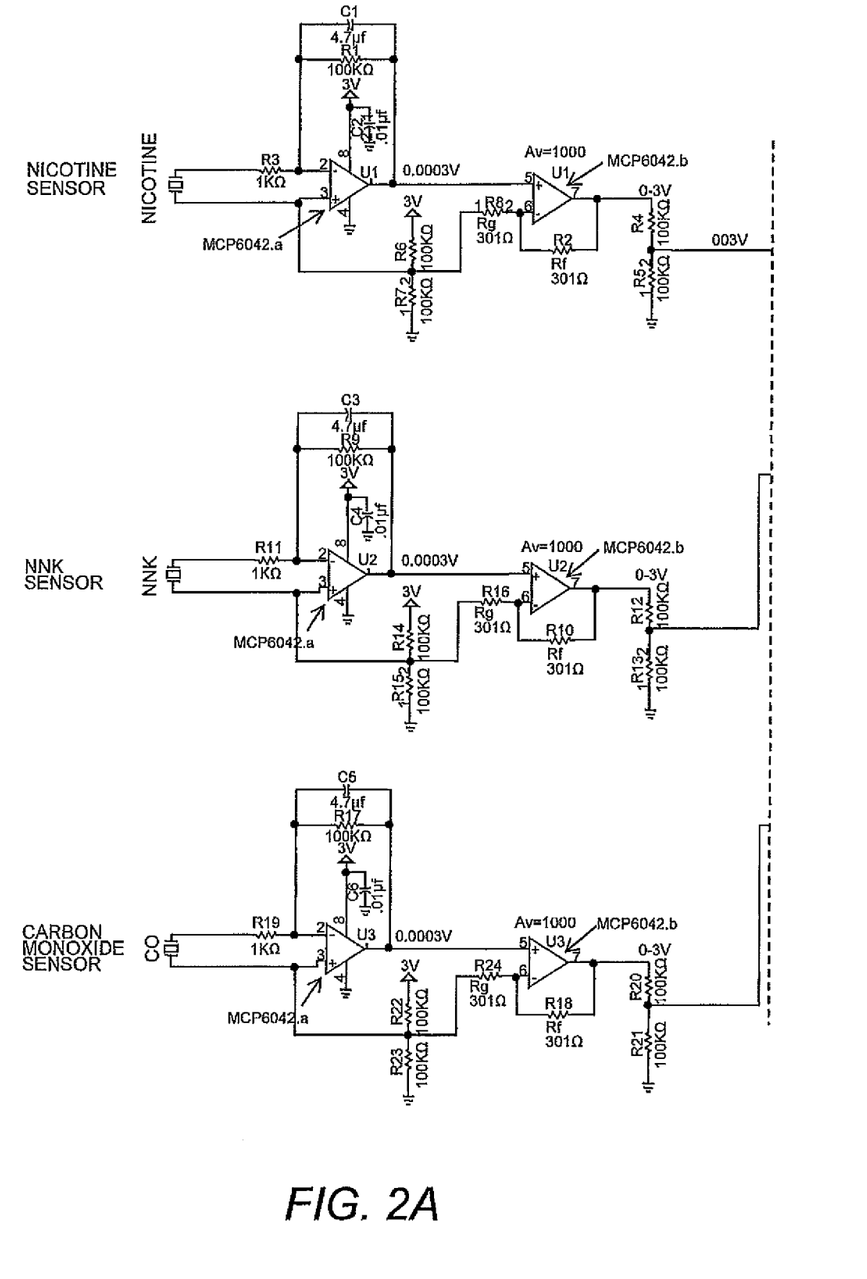
FIG. 2 is a schematic drawing showing sensor placement over the circuit.
Figure 2B:
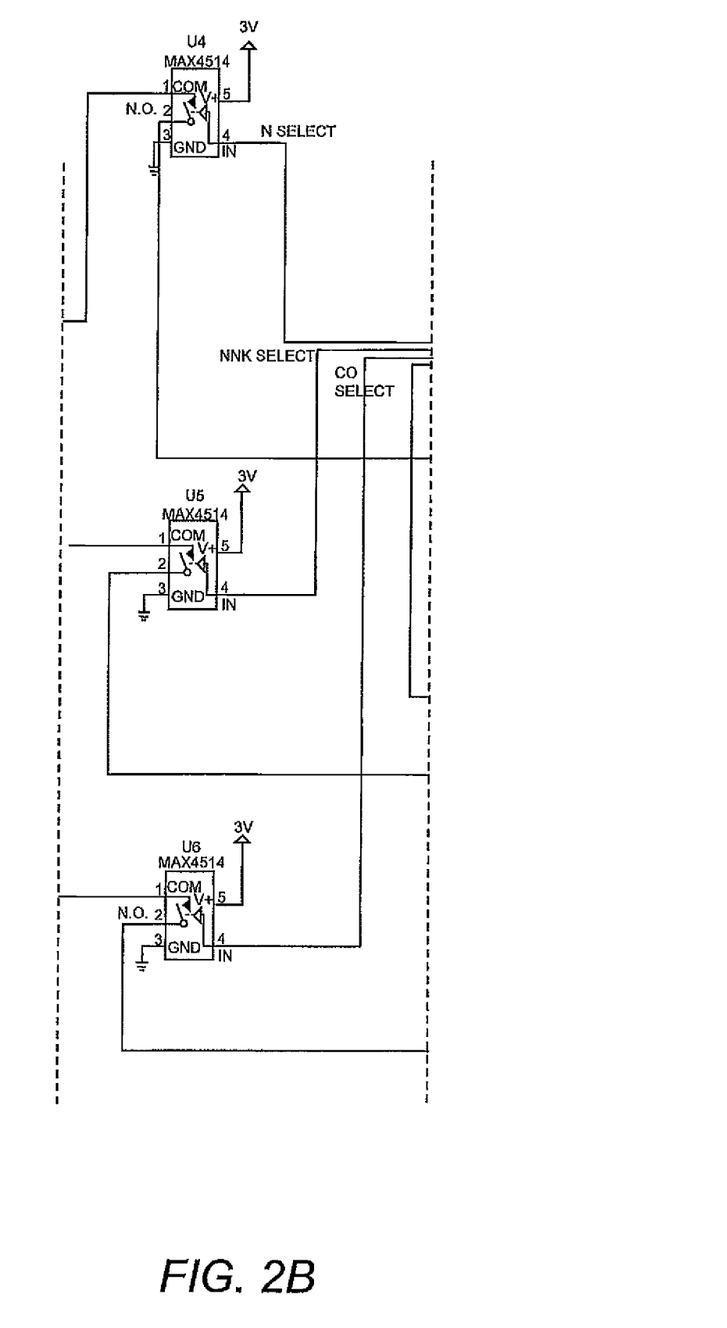
Figure 2C:
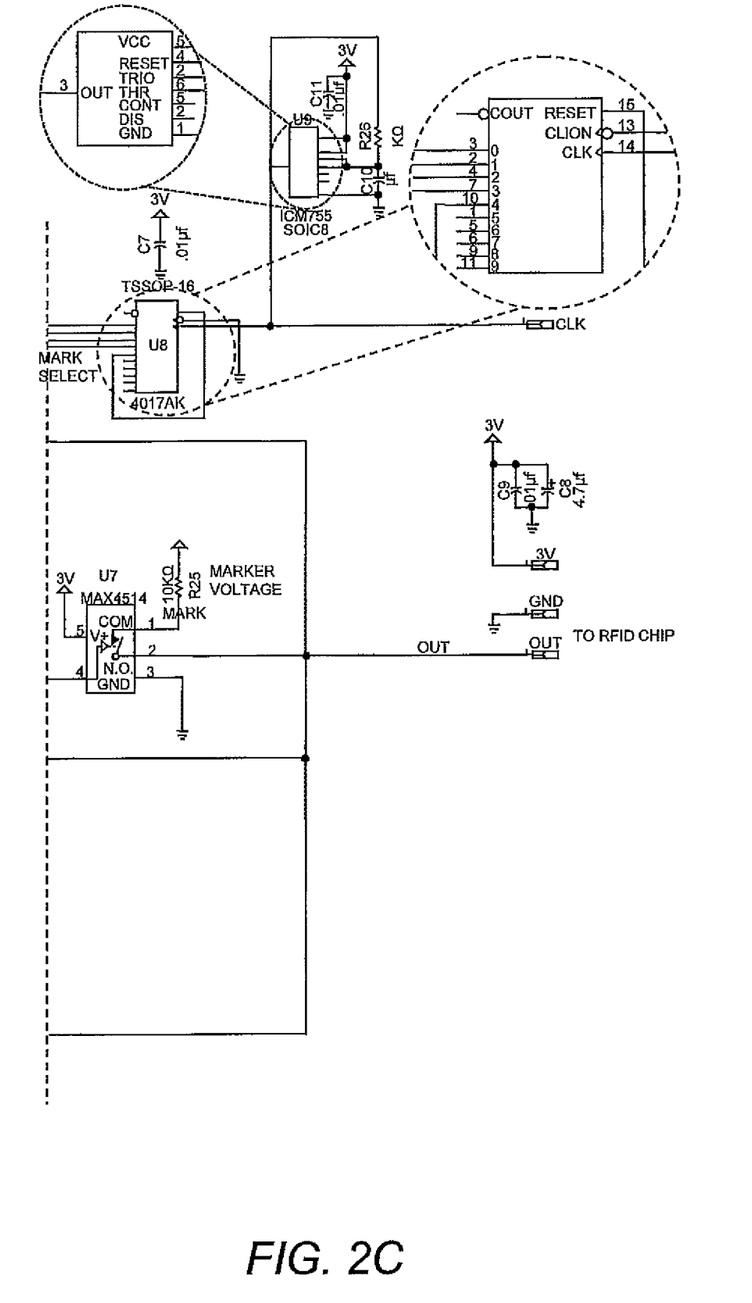

To remotely communicate the output of the sensors, the device further includes a radio frequency interrogator unit. Such interrogator units typically include an antenna, and transmit an interrogation signal or command via the antenna. The instant device can operate over a wide range of carrier frequencies. For example, the device can operate with carriers of 915-5800 MHZ, wherein the frequency selectivity is based on selection of the antenna. Moreover, in so far as the device employs one or more MIP films to simultaneously detect multiple airborne contaminants, the device further includes multiplexing RFID circuitry. The sensors of the instant device have a range of values and the interrogator unit must be capable of reading two or more separate sensors (FIG. 1). As such, in certain embodiments, the instant device also has a multiplexing amplifier circuit that includes on-board memory to store values. This includes assembling on-board memory and addressing hardware and certifying the operational status before calibration of the final device to assure that the assembled sensor functions within the same parameters as the individual components. An example of an RFID circuit of the instant device is shown in FIG. 2.

Interrogator units also generally include dedicated transmitting and optionally receiving circuitry. Active transmitters are known in the art. See, for example, U.S. Pat. No. 5,568,512, which also discloses how the transmit frequency for the transmitter is recovered from a message received via radio frequency from the interrogator. Moreover, many examples of wireless communications circuits are known in the art, and any suitable low-power circuit may be employed. The invention is intended to be practiced with any radio communications circuit with low power requirements, for example, a circuit appropriate for extended operation in a remote battery-powered device without need for recharging.

The device of the invention can transmit radio frequency signals to a receiver and/or host computer in communication with the interrogator. An exemplary receiver includes a conventional Schottky diode detector. When a host computer is employed, the host computer can act as a master in a master-slave relationship with the interrogator. The host computer can include an applications program for controlling the interrogator and interpreting responses, and a library of radio frequency identification device applications or functions. Most of the functions communicate with the interrogator.

Although sensor systems described herein are particularly suitable for efficient operation by conventional power sources used in portable/remote electronics (e.g., battery, solar cell, miniature fuel cell), the instant device can also use alternative energy resources, such as a thermocouple, radiofrequency energy, electrochemical interactions, supercapacitors, energy scavenging mechanisms, or the like, or combinations thereof.

In so far as the device can detect airborne contaminants such as CO, nicotine, 4-(methylnitrosamino)-1-(3-pyridyl)-1-butanone and/or formaldehyde, the device of this invention is of particular use in monitoring exposure to secondhand tobacco smoke. Upon exposure of the device to an air sample, the molecular imprinted films bind airborne contaminants in the air sample, sensors of the device sense said binding, and radio frequency signals are transmitted to alert the user of exposure to the airborne contaminants.

While conventional technologies can measure nicotine and particulate matter in indoor environments, the current technology involves large air sampling devices and hinders the process of immediate feedback, since complex procedures are required, in an analytical laboratory, to quantify the samples. Moreover, the sampling technique collects all airborne material and the analytical instruments are required to sort out the adsorbed material. The device is unique in that it is small (personnel badge sized), easy to read, simple (no laboratory analysis is needed), the MIP films are targeted to specific contaminants and a number of contaminants can be simultaneously detected. As a wall-mountable or wearable, personal badge-type, second-hand smoke detector, the instant device finds application in, e.g., medical centers to monitor the environment of pediatric (and other) patients, and to measure tobacco smoke contamination in supposedly smoke-free environments such as hotel rooms and rental cars. Since the specific sensor in the monitor may be readily changed to monitor a different air-borne contaminant, the instant device can be adapted to detect an array of different molecules or hazardous vapors.

The invention is described in greater detail by the following non-limiting examples.

Example 1

Production of PVP MIP Films

The aromatic nature and hydrogen bonding potential make Poly(4-vinylphenol) (PVP) an ideal host matrix for MIPs. The PVP films were produced by spin coating; a simple deposition technique that is sensitive to the composition and viscosity of the solution and the rotating speed of the plate (Bronside, et al. (1987) *J. Imaging Technol.* 13:122).

Solutions composed of 10 mL of methanol (Acros Organics; ACS Reagent Grade 99.8%) with 10 wt % of PVP powder obtained from Polysciences, Inc. (MW-22,000; $T_g$ 150° C.) and 5 wt % of nicotine or cotinine were nitrogen purged, covered, and stirred at room temperature for 24 hours. Control films (NIPS) were similarly produced, but without the nicotine or cotinine. Films were spin cast from these solutions onto 22 mm square glass microscope cover slips. Typically, the slides were prewashed with spectroscopic grade isopropanol and acetone prior to polymer deposition. The coating solution was dropped onto a stationary substrate and the spin coater was operated at 4000 rpm for 30 seconds with negligible ramp up time. The rotation spreads the solution evenly over the surface and also causes the solvent to evaporate leaving a thin film of material on the substrate. The concentration of PVP in the casting solution is the dominant variable for the film thickness, which increases rapidly with increasing concentration (solution viscosity). Cast films are quite stable and may be stored or used for an indefinite time.

The template molecule was removed from the film by immersion in deionized water for five hours. Nicotine (or cotinine) removal was confirmed by FTIR measurements. Template reinsertion (or reinsertion of the complementary template molecule) was accomplished by immersion of the template extracted (or control) film in a 5 wt % solution of the molecule in deionized water for 2.5 hours. This reinsertion, as with the template removal procedure, is an equilibrium-controlled process and reinsertion occurs to approximately 50% of the initial concentration (via qualitative FTIR measurements). Additional immersion time was not found to increase the relative amount of template molecule reinserted into the film. FTIR spectra were recorded over a narrow region of interest, ~3400 cm$^{-1}$ for the OH stretch of PVP, which is missing when hydrogen bonded to nicotine or cotinine or ~1700 cm$^{-1}$ in the carbonyl region of cotinine, to confirm the interaction of the template with the polymer in the film. The surface topography of the films is characterized by average roughness measurements, $R_a$, using scanning force microscopy (SFM). It is defined as the average deviation of the profile from a mean line or the average distance from the profile to the mean line over the length of the assessment. The surface roughness, $R_a$, is given by the sum of the absolute values of all the areas above and below the mean line divided by the sampling length.

All nanoindentation experiments were performed using the electrostatic transducer of the Hysitron triboscope in the UBI 1 (Hysitron User Handbook: Feedback Control Manual. 10025 Valley View Road, Minneapolis, Minn.; Hysitron, Inc.). The transducer is a three-plate capacitor, the mid-plate of which carries the indenter fixed to a thin stylus. Application of a DC voltage generates an electrostatic force driving the indenter into the sample surface, while the capacitance change as a measure of penetration depth is recorded. The data consist of a force-displacement curve. For soft samples such as polymers, the stiffness of the internal springs holding the indenter must be subtracted from the applied load in order to obtain the sample stiffness. Hardness, H, is calculated as the applied load, F, divided by the area, $A_c$, of the indenter tip at the contact depth, $v_{hc}$; the area is depth-dependent (Olivier & Pharr (1992) *J. Mater. Res.* 7:1562). The modulus is derived from the slope of the force-displacement curve upon unloading when the sample elastically recovers. The tip elastic properties can effectively be ignored for polymeric materials. Investigations are performed with a blunted 90° diamond cube corner tip. The calibration of the tip to determine the depth dependent area function $A_c(hc)$ was obtained with the standard curve-fitting method using fused quartz with its known reduced modulus as the reference material. Additionally, calibration with a sharp silicon grating was performed (Richter, et al. (2006) *High Pressure Res.* 26:99). A commercial grid with ultra sharp conical silicon tips was used. The small apex angle of the grid tips (below 20°) together with their large height (700 nm) offers the opportunity for exact examination of the shape of the diamond indentation tip apex. By means of the AFM software using the so-called bearing function, the shape of the diamond indenter can be reconstructed and the area function $A_c$ can be obtained. The advantage of this technique over the curve-fitting method is the direct observation of the tip shape, which also allows the estimation of the blunt tip radius, which was 600 nm in our experiments.

Thermal drift and creep behavior of the piezoelectric scanner must be minimized. At the nanoscale, drift is measured and compensated in the resulting data. This compensation factor is part of the standard UBI software and a correction measurement is performed before each indent. Typical drift rates range up to 0.5 nm/s. The penetration depth of the indent should not exceed 30% of the polymer film thickness to avoid substrate effects. Most experiments were performed with smaller penetration depths, however depth-dependent measurements sometimes show an increase in hardness and reduced modulus with increasing penetration indicating the influence of the glass substrate.

Depth-dependent mechanical properties are obtained through indentation tests where repeated loading and unloading are performed at the same location on the sample surface (Richter, et al. (2006) *Colloids and Surfaces, A* 284/285:401; Fischer-Cripps (2002) *Nanoindentation*, Springer, New York; Olivier & Pharr (1992) supra; Wolf & Richter (2003) *New J. Phys.* 5:15.1; Maier, et al. (2002) *Mater. Character.* 48:329; Ward & Hadley (1993) *An Introduction to the Mechanical Properties of Solid Polymers*, John Wiley & Sons, Chichester; Nowicki, et al. (2003) *Polymer* 44:6599; Du, et al. (2000) *Polymer* 42:5901; Drechsler, et al. (1998) *Appl. Phys.* A66:825; Tsui, et al. (2000) *Macromolecules* 33:4198; VanLandingham, et al. (2001) in: Tsukruk & Spencer (Eds.) *Macromolecular Symposia*, Wiley-VCH Verlag, Weinheim, pp. 15-43). Eight cycles of multi-indentation were performed to calculate the depth-dependent hardness and the indentation modulus. In general, multi-cycling means, after loading to a maximum load, $F_{max}$, the sample is partially unloaded to a minimum load, $F_{min}$=0.1 $F_{max}$ to 0.25 $F_{max}$, required to prevent the tip from losing contact with the sample and sliding to a new lateral position. The sample is then reloaded to the same or an increased maximum load ($F_{max}+\Delta F$) and the cycle is repeated. After the onset of plastic deformation, the loading curve is an overlap of both plastic and elastic deformations. Multi-cycling delivers a set of data that includes the entire material response, from the first indenter-sample contact to the maximum penetration.

Computational Details. All optimizations were performed with NWChem, a Computational Chemistry Package for Parallel Computers, v5.1, with no symmetry or geometric constraints. The correlation and exchange effects were calculated using the Perdew-Burke-Ernzerhof (PBE) exchange-correlation functional (Adamo & Barone (1998) *J. Chem. Phys.* 110:6158) with the 6-31G* basis set (Hariharan & Pople (1973) *Theoret. Chimica Acta* 28:213) both for all atoms. Several relative orientations of the PVP molecule(s) relative to nicotine or cotinine were optimized to ensure that the total energy of the complex was not dependent upon this factor. All calculations were run in parallel on a Linux cluster composed of 94 Quad-Core (2×) AMD Opteron nodes (752 cpus), and 6 Quad-Core (2×) Intel nodes (48 cpus). In aggregate, the Linux cluster had 3 terabytes of memory and more than 35 terabytes of disk space. Geometric structures were visualized using the AVOGADRO molecular editor program.

Example 2

Nanohardness Analysis of Nicotine- and Cotinine-Imprinted Poly(4-vinylphenol) Films Control PVP and MIP Film General Features. The structure of the MIP and NIP films was dependent on the viscosity of the solution. This was mainly controlled by the temperature and spin casting conditions such as speed and deposition time, in addition to the PVP concentration in the solution. The pure PVP films deposited from the casting solution containing 10% polymer had a characteristically smooth morphology. In the present analysis, the pure PVP film had a surface roughness, $R_a$, of 11.5 nm, over a 130 µm×130 µm sample. No significant morphological features were found in the control PVP films; the films were flat. The 'as produced' MIP films containing, for example nicotine template molecules, showed a different surface morphology in comparison to the control films. Surface stripes, representing different heights, were the main surface feature. The surface roughness of this type of sample was measured to be 69.2 nm, over the same 130 µm×130 µm sampling size. Removal of the nicotine from the MIP resulted in a loss of the stripe morphology and the observation of a number of pores in the surface. The pores were apparently formed during the solidification process of the polymer films and were caused by the presence of the template molecules and the porogen solvent during the film growth process (Campbell, et al. (2009) supra). The assumption was that the pores were present in the 'as produced' samples, but lay beneath the stripe morphology. The template molecules were smaller than the size of the pores observed in the films. The additional volume of the measured pores resulted in part from: the geometrical form of the template molecule, the arrangement of that molecule within the polymer host, and the evaporation of the solvent through the polymer film. The surface roughness $R_a$, of the nicotine-removed MIP was 44.1 nm, over the 130 µm×130 µm sample. Reinsertion of nicotine into this MIP restored the strip morphology somewhat, but had minimal effect on the roughness of the surface ($R_a$=33.1 for the 130 µm square sample). The different film morphology in the SFM images was characteristic for the presence of the template molecules.

Nanomechanical Properties.

The contact pressure (hardness) can vary even for homogeneous matter such as the control sample, since the deformation starts with purely elastic deformation, and after yielding, the plastic contributions increase after a saturation value of H is obtained for very large indents. This means the hardness decreases with increasing indentation depth. Within the indentation size effect model (Wolf & Richter (2003) supra) the hardness will be higher in a small indentation area where fewer defects are encountered. With increasing indentation size (depth), more defects such as dislocations, are generated by the contact pressure. For very thin polymer films, the indentation modulus is not constant due to the increased substrate influence with increasing depth. The elastic behavior of pure PVP films occurs by deformation of the polymer molecules and movement of the chains after the adhesion energy has been overcome.

The multi-cycling load-depth curves for MIP films with template molecules in the casting solution for the spin coating process showed significant differences in comparison to pure PVP films. From the load-depth curves, it was clear that the 'as produced' nicotine-loaded MIP films had indentation depths of approximately 175 nm with a maximum applied force of 300 µN; removal of the nicotine increased the penetration depth to nearly 200 nm. Unexpectedly, reinsertion of nicotine reduced the penetration depth to a value 35 nm less than the original imprinted film. Clearly, the presence of the template molecule in the MIP led to a stiffer film and analogous results were recorded for cotinine imprinted films. The assignment of the basis of the change in nanomechanical properties to the template was reinforced by the fact that the MIP with the template removed was less stiff than a pure PVP film for the same applied force.

The nanomechanical behavior of the polymer films indicated that hardness decreased slightly with increasing depth, whereas the indentation modulus increased slightly with increasing depth. The hardness of the control PVP film had the value of 0.38 GPa with an indentation modulus of 11.7 GPa. MIP films with cotinine were stiffer with a hardness value of 0.59 GPa and an indentation modulus of 14.7 GPa. Nicotine imprinted films were slightly stiffer than the control film with a hardness value of 0.43 GPa and a modulus of 11.6 GPa. Extraction of the template molecules meant that the molecular cavities were still in the polymer matrix, but the space was empty. Thus, the network character and therefore the mechanical properties changed. For example, the hardness for MIP films with nicotine extracted yielded smaller values of 0.31 GPa for the hardness. Reloading of either template resulted in an increase of the hardness to values greater than those of the original 'as produced' MIP films. The percentage increase in hardness was greater for the reinsertion of nicotine into a nicotine-targeted MIP than for cotinine into a cotinine-targeted MIP. Loading, extraction and reloading of nicotine or cotinine in the MIP films were clearly measurable with the nanoindentation method.

These results indicate a strongly hydrogen-bonded network between the polymer chains via the template molecules. In the ideal case, the molecular cavities with nicotine template molecules were formed by two hydrogen bonds that cross-linked between two PVP molecules; cotinine had three such potential hydrogen bonding sites. However, the imprinting process could be incomplete with fewer hydrogen bonds established. Template molecules can bond to the polymer molecule at several points along the chain with efficiencies dependent on the number and distribution of template molecules in the MIP film. From the nanomechanical investigations it was contemplated that hydrogen bonds of the template molecules between the PVP chains resulted in a cross-linking between the chains, separated the PVP molecules, (preventing an easy movement of the chains, and could reduce the adhesion energy between pure PVP molecules. This could result in either, mechanically stiffer or softer MIP networks. Two different molecular mechanisms were proposed for the polymer response during an applied external contact pressure. In pure PVP, the indentation tip could cause a deformation of the PVP molecules and a sliding motion between the chains. The molecular cavities and micro-pores change the mechanical properties in two directions compared to pure polymer films. Filled cavities (template-loaded MIP) showed an increase in hardness in comparison to pure PVP films. This meant a stiffer molecular network was established. In MIP films, the chains are fixed by hydrogen bonds and the sliding motion is inhibited in general. The filled molecular cavities prevent strong elastic deformation. Empty cavities after extraction of the template, result in a large decrease in the hardness. This could be caused by the fact that the empty MIP network can be easily squeezed together, resulting in a lower hardness in comparison to the pure polymer network. In MIP films, the PVP chains are fixed by the hydrogen bonds and the formed molecular cavities, but the deformation around the empty cavities is flexible (breathing cavities). Therefore, no gliding motion of the chains occurs. This means, the main effect for the change of the mechanical properties in different stages of MIP films originates from the formed molecular cavities. If they are filled with the template molecule the material is harder; if the cavities are empty, the compression of the cavities leads to a much softer material. The elastic compression of the empty cavities and pores acts in the same direction as the mechanism of deformation and gliding of the PVP chains.

Computational Study of Hydrogen Bonding.

Reports in the literature indicate the usefulness of computational chemistry in selecting a polymer host for MIP development with a particular target molecule (Breton, et al. (2007) *Biosens. Bioelectron.* 22:1948). However, it was contemplated that computational studies would be of use in providing information to understand experimental MIP results. The optimized structures of nicotine and cotinine were first obtained for reference. These molecules differ only by the addition of a carboxyl group on the pyrrolidine ring of cotinine. The geometry of the planar pyridine ring, including bond lengths, in the two molecules is identical. The presence of the oxygen atom in cotinine results in bond shortening in the pyrrolidine ring, as well as a further distortion from planarity relative to the nicotine pyrrolidine ring. The pyrrolidine nitrogen becomes more sp2-like rather than the pyramidal angle observed in the nicotine molecule. As a final reference point, the 4-vinylphenol dimer structure was optimized and was found to have a hydrogen bond length of 1.876 Å and a hydrogen bond energy of 0.34 eV. The geometric parameters of the 4-vinylphenol molecule were unchanged in the dimer.

Nicotine has two potential hydrogen binding sites and cotinine has three such sites. In both clusters, the 4-vinylphenol geometry was identical to that of the unbonded molecule and the pyridine rings bond lengths were unaffected by the hydrogen bond. The hydrogen bond from 4VP to the pyridine nitrogen in nicotine had a length of 1.822 Å, while that to the pyrrolidine nitrogen was 1.788 Å. The C—N bond lengths in this ring both increased. The total hydrogen bonding energy was 0.84 eV. In cotinine, only two hydrogen bonds formed. The bond to the pyridine nitrogen had a length of 1.820 Å and that to the carboxyl-oxygen was 1.784 Å with a total hydrogen bonding energy of 1.00 eV. Attempts to add a third hydrogen bond at the pyrrolidine nitrogen site failed, as the additional PVP molecule was repulsed from the ring. The C—N bond lengths in the pyrrolidine ring both decreased upon hydrogen bonding. Finally, it was noted that attempts to obtain a π-π complex between cotinine and 4VP indicated that the ring interactions were repulsive. Clearly, the DFT calculations indicated that cotinine would complex to the PVP host matrix with a greater binding energy than would the nicotine template and the experimental results reflected the results of those calculations.

Example 3

Preparation of Polyaniline-Nylon Films

Polyaniline has the general structure:

Polyaniline was selected for the film given its conductivity (Scheme 1).

Using phase inversion, formaldehyde cavities were created in a polyaniline (PANI)-Nylon 6 composite film. Films were produced by dissolving 0.2 g of PANI, 0.2 g of Nylon 6 and 200 µl of formaldehyde in formic acid. The formic acid dissolved the composite and formaldehyde to form a rigid polymer-formaldehyde network. After sufficient mixing, the imprinted polymer solution was uniformly spin-coated onto a glass substrate to form a thin film. After making the formaldehyde imprinted films, the formaldehyde molecules were extracted from the film aerially, leaving behind formaldehyde-specific receptor sites that were capable of molecular recognition and binding of formaldehyde molecules with remarkable specificity.

Infrared spectra analysis conclusively indicated that formaldehyde molecules could bind to the PANI-Nylon 6 composite through strong hydrogen bonding due to the presence of an elongated carbonyl group at 1722 $cm^{-1}$. This peak was present in the imprinted polymer composite and noticeably absent in the control. This analysis indicated that PANI-Nylon 6 was successfully imprinted with formaldehyde. Moreover, the intensity of the peak indicated the efficacy of the imprinting process.

Changes in electrical resistance of imprinted polymer and control polymer following controlled exposure to formaldehyde vapor were determined using lithographically patterned interdigitated electrodes. The results of this analysis indicated that because the imprinted polymer had formaldehyde-specific cavities, it was able to selectively adsorb the formaldehyde molecules, which caused a dramatic increase in resistance of the film. In contrast, the control film with no cavities exhibited a relatively insignificant increase in electrical resistance in response to the formaldehyde vapor.

Example 4

Preparation of Polyaniline Films in Sensors for Detecting Nicotine

Materials and Methods.

Polyaniline was purchased from Polysciences, Inc. as the undoped emeraldine base form with a molecular weight of 15,000 and a conductivity of $10^{-10}$ S/cm. Formic acid, >98%, was purchased from EMD Chemicals and used to dissolve the polyaniline prior to spin casting. Secondary doping increased the sensitivity of the films and HCl, purchased from Fisher Scientific (ACS Certified), was used in a 1.0 M aqueous solution. For laboratory studies, nicotine purchased from Alfa-Aesor, 99%, was used. All reagents were used as received without any further treatment. The standard cigarettes used in the smoking chamber were 3RF4 reference cigarettes, containing ~0.8 mg of nicotine.

The polymer films for detecting nicotine were spin-cast polyaniline. Polyaniline in its conductive form is insoluble. However, the emeraldine base may be dissolved in several solvents, including the 98% formic acid used herein. The spin casting solution was produced from formic acid as a 1% (by weight) polymer solution. Because the p$K_a$ of formic acid is 3.77, polyaniline in this solution was 50% protonated; the amine and imine nitrogen atoms had different p$K_a$ values. To complete the protonation process and increase the sensitivity of the film, secondary protonation in 1.0 M HCl was employed. Protonated solutions are green, while solutions of the base are deep blue. Morphology and roughness were investigated by atomic force microscopy using a Pacific Nanotechnology Nano-1 microscope in close contact mode.

The conductive sensors were constructed on oxidized silicon substrates using chromium metal with a nickel overlayer for the electrode and the protonated polyaniline film as the active element above the electrode. The electrode was patterned into an interdigitated grid with 40 µm fingers and 20 µm spacing.

Prime grade silicon wafers with a 5000 Å thermally deposited oxide layer were used for the substrate. These films were patterned by photolithography and subsequently wet-etched to produce the final electrodes with a total area of 376 mm$^2$, following vapor deposition of 200 Å of chromium and a 1000 Å overlayer of nickel. Liftoff was accomplished using acetone, with final rinses of water.

Subsequently, the polyaniline polymer layer was spun on the sample. An aliquot of 0.5 ml of solution was dropped onto the substrate (oxidized silicon), and allowed to spread for 20 seconds. The spin-coater was then brought up to 4000 rpm for 30 seconds. This resulted in deposition of films with a typical thickness of approximately 100 nm. In the final step, secondary doping with 1.0 M HCl was accomplished by dip-coating for 30 seconds. After this treatment, background (washed) resistance values were measured, and the sensor was ready for use in binding studies.

Smoking machine experiments were carried out in a Teague Enterprises package (Teague Enterprises, Davis, Calif.), composed of a TE-10 smoking system and a mouse exposure system. The smoking device was microprocessor controlled and produced both mainstream and sidestream (separately or simultaneously) smoke from filtered research cigarettes produced with controlled nicotine content. Up to ten cigarettes could be smoked simultaneously following the Federal Trade Commission procedure and expended cigarettes could be automatically extinguished and ejected. Smoke was captured and transferred to a mixing chamber for exposure experiments; sidestream or mainstream smoke was mixed with air and then passed into the exposure chamber. However, for the experiments described here, the system including sample lighting and extinguishing was operated in manual mode. A filter was available for venting and purging the system. The exposure chamber was calibrated for total suspended particles (TSP), carbon monoxide and nicotine concentration determined for selected mixing valve and fan settings. All measurements using the Teague Enterprises system were made with the polymer sensors in the exposure box, using calibrated operational parameters.

The laboratory sample system was composed of a small nylon box, containing spring-mounted electrodes and a small (~3 cm$^3$) well filled via a syringe through a septum. The sensor assembly was placed on the electrodes above the well and a nylon cap was attached using a torque wrench to ensure reproducible pressure of the sensor against the spring-mounted electrodes. Nicotine (1 mL) was injected into the well and the response of the sensor was recorded. To follow the recovery of the sensor after exposure to nicotine, dry nitrogen was passed through the well to evaporate the nicotine. In both experimental chambers, the change in the resistance of the sensor was measured using a multimeter connected to a laboratory computer.

The resistance, R, of the polymer sensor was measured using a Keithley Model 2100 6½ Digit Multimeter. During the measurement, constant current of 1 mA was applied and the voltage through the film was recorded, providing a resistance value via Ohm's law. Total dissipated power within the sensor was less than 2 W. Four point measurements were found unnecessary and all of the reported data were obtained using two contacts. Data were taken at a rate of 1 Hz over as long as 9 hours, but typically over considerably shorter times. The resistance increased from its low background value prior to exposure, typically 600Ω, through to a plateau, associated with the level of nicotine in the sample chamber. Data are reported as normalized resistance, referenced to the initial, out of chamber background value.

Films were exposed to analyte concentrations that ensure a challenge to the adsorption process. The results provided an indication that the shift in the resistance value and the rate of change in the resistance, were proportional to the quantity and identity of the analyte adsorbed.

Results and Discussion.

The morphology of the film surface was investigated by atomic force microscopy (AFM) of films produced on both silicon oxide and glass under the coating conditions described above. The undoped film was rougher than the doped material and more irregular with surface defects. The doped film was somewhat smoother and the minimal occurrence of surface defects provided an ideal material for adsorption of the target molecule from the vapor phase.

The physical property associated with the target molecule presence in the film was the increase in the resistance. Sensor functionality depended upon detecting differences in this property as a function of the adsorption of the target nicotine onto the sensor chip. Numerous films were tested using both pure nicotine in the small lab-built chamber and nicotine emitted from cigarette consumption as measured in the Teague smoking system. Data presented here are typical of these observations.

Figure 3A:
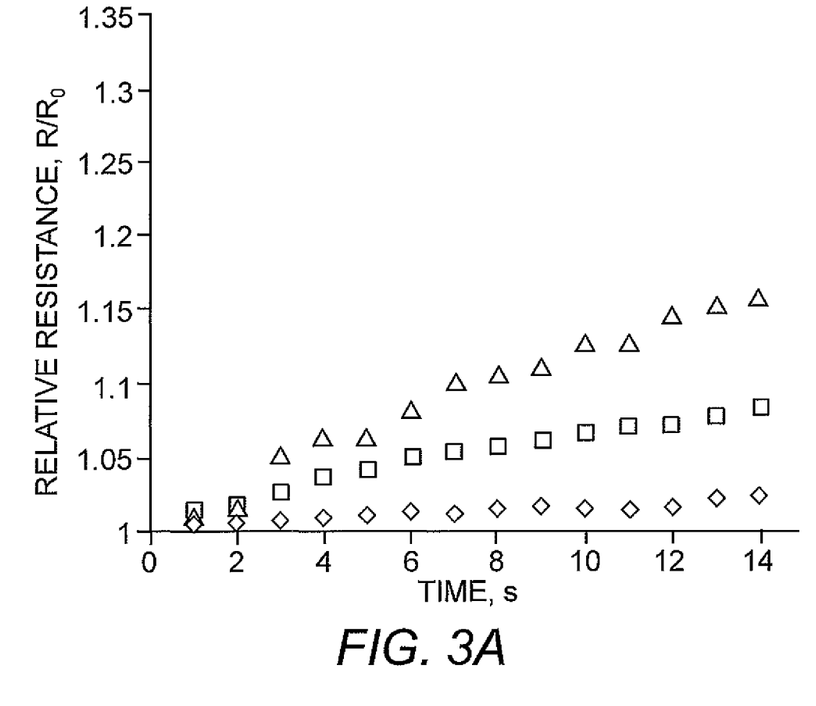
FIG. 3A shows the response of the sensor to vapor phase nicotine from liquid nicotine held at a series of different temperatures; diamond=22° C., square=55° C., triangle=80° C.
Figure 3B:
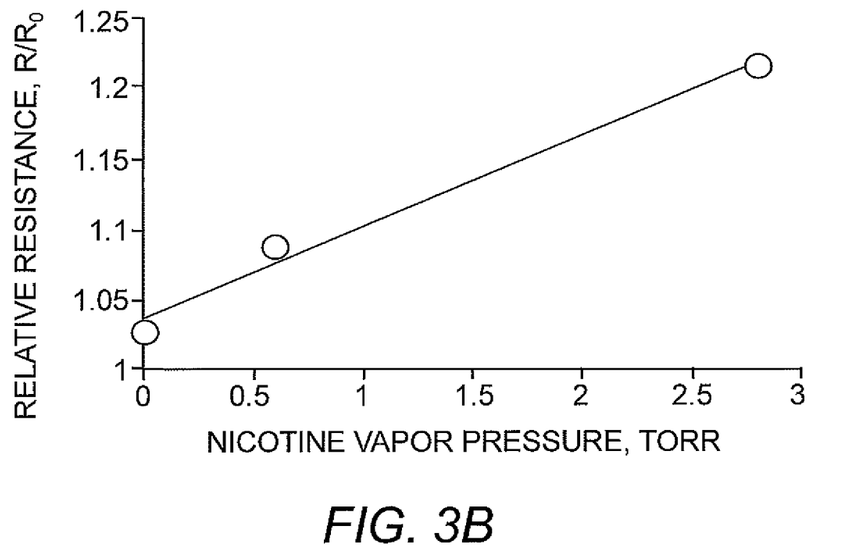
FIG. 3B shows a plot of signal as a function of nicotine vapor pressure.

Testing of the sensor in the laboratory chamber indicated that injection of nicotine into the sample well evoked an immediate rise in the measured resistance. Nicotine vapor pressure was quite small at room temperature, so a series of experiments, injecting nicotine at different initial temperatures (providing different vapor pressures and, hence, vapor phase concentrations of nicotine in air) and recording the resistance was completed. The relationship of nicotine vapor pressure to sample temperature is well established and was used in this analysis (Young & Nelson (1928) *Ind. Eng. Chem.* 20:1381-1382). The results of this study are shown in FIG. 3A for three different nominal temperatures. For example, consider the film response to the injection of nicotine at a nominal 80° C. The rise of the signal as the sample was injected and the beginning of a plateau of the signal (and slight decrease) as the sample cooled was clearly demonstrated. FIG. 3B shows a plot of the signal (15 seconds post injection) as a function of the nicotine vapor pressure at the nominal temperatures. A linear fit to the data with a correlation coefficient of 0.99 is shown. The nicotine began to cool almost immediately, therefore, deviation of the fit from an exact correlation with temperature was to be expected. The absence of constant temperature capability in this device precluded its use as a calibration system. However, the trend of increasing resistance with increasing temperature was clear and demonstrated the responsiveness of the film to pure nicotine. The nicotine concentrations in this device were estimated to be of the order of a few ppm.

Figure 4:
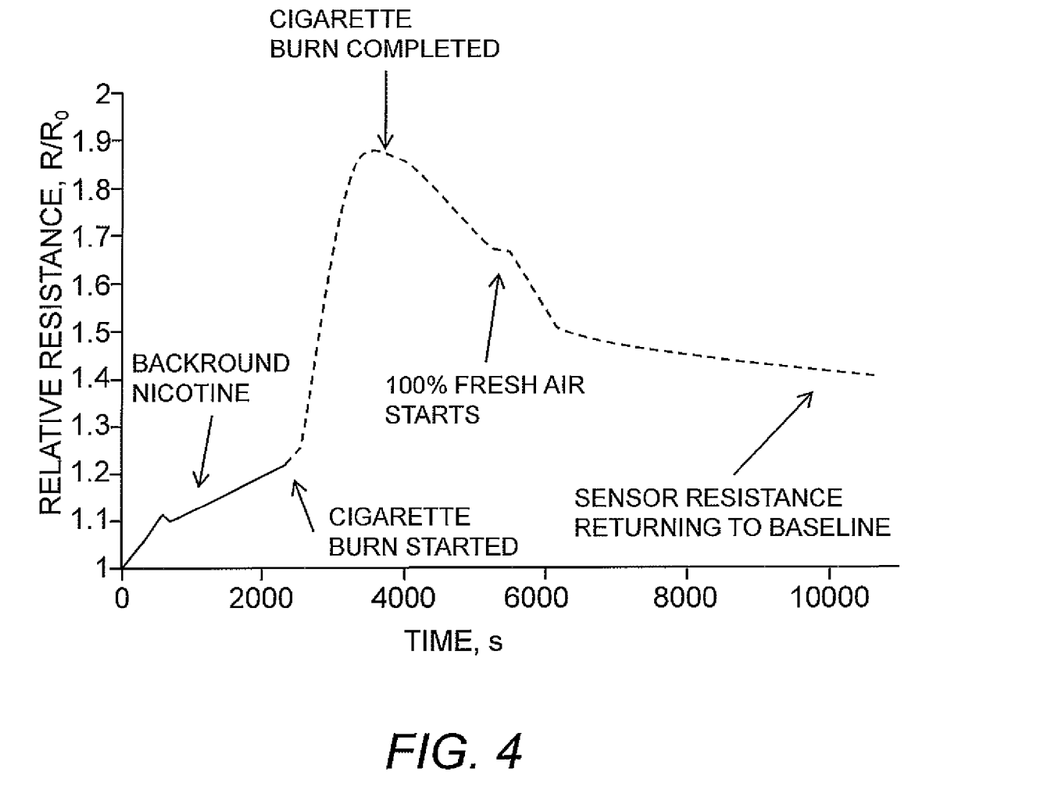
FIG. 4 shows the response of the sensor in terms of relative resistance to exposure of vapor phase nicotine generated from a single cigarette in the Teague system. Note also, that the sensor detects nicotine adsorbed on the walls in the chamber from previous experiments, so called third hand smoke.

FIG. 4 shows the time evolution of the sensor film signal for smoking a single cigarette in the Teague system. The system calibration at the inflow/outflow settings of the exposure chamber provides that the dynamic nicotine concentration in this situation from the cigarette consumption alone was 0.5 ppb. The actual concentration was, of course, higher since there was clearly background nicotine adsorbed onto the chamber surface. In general, the resistance increased as the cigarette was consumed, increasing by 50% over the signal assigned to the chamber background. It was interesting to note that the background reading of the sensor, the resistance at the zero time point, immediately increased by 20% as the film was placed into the exposure chamber, indicating a background level of nicotine before engaging the smoking apparatus. Prior to this experiment, the smoking chamber had been in constant use for 8 hours and deliberately not cleaned in the 2 hours prior to its application in the current experiment. The sensor was capable of measuring nicotine that was outgassing from the plastic chamber walls, an event labeled as "third hand smoke" when this event occurs in inhabited rooms and automobiles (Sleiman, et al. (2010) *PNAS* 107:6576-6581). During the smoking process, sidestream smoke was fed into the exposure chamber and, as long as the smoking was continued, the resistance increase indicated adsorption of nicotine in to the film. The signal stopped increasing as the cigarette was extinguished and decreased as air blown into the exposure chamber from the smoking system contained no additional nicotine component. After approximately six minutes, the chamber was purged with 100% fresh (room) air and the sensor resistance dropped accordingly to a level approximately 20% above the chamber background.

A set of sequential exposures in the Teague system, using varied number of simultaneously smoked cigarettes followed by a brief fresh air blowout was conducted. Cigarettes were smoked over a period of eight minutes during which the sidestream smoke filled air from the smoking device was mixed with an equal volume of fresh air and fed into the exposure chamber. Following the extinguishing of the consumed cigarette, fresh air was blown into the exposure chamber for a period of six minutes. The fresh air phase was shown to allow at least some of the nicotine to be removed from the sensor and restore the resistance measurement to a smaller value. These two different regimes were clearly discernible. The fresh air phase of the repetitive experiment was not sufficient to bring the sensor back to the original baseline. That is, the process of removing the nicotine from the film was slower than the time used in the study and subsequent exposures included increased residual levels of nicotine from the walls of the chamber in addition to nicotine that remained on the sensor film from the previous cigarette consumption. However, the final exposure cycle, with a longer smoke-free period, indicated that a return approximately to the original baseline was possible. Indeed, a resistance measurement made several hours after completing the experiments resulted in a value nearly equal to the initial resistance. The slopes of the rising signals were also related to the number of cigarettes simultaneously consumed and, hence, the concentration of nicotine in the chamber. The system provided a dynamic concentration of 0.75 ppb and 1.11 ppb, for sidestream smoke generated solely by two and three cigarettes, respectively. But as described earlier, this underestimated the true nicotine concentration. It was noted that the first, single cigarette consumed increased the signal by ~60% and second, consecutive single cigarette furthered the increase by 32%. The next sample involved two cigarettes and resulted in a 40% signal increase with a final sample of three cigarettes and a 42% increase in resistance. The "blow out" phase returned the signal to approximately the resistance measured after the first experiment.

To test the response and recovery in a heavy smoking situation, several successive runs were conducted in which cigarettes (nominally providing 3.16 ppb of nicotine) were simultaneously smoked. The sensor background resistance was measured in ambient room air prior to insertion in the exposure chamber, providing a clear visualization of the ability to detect nicotine from the chamber walls. The first cigarette burn resulted in a steep increase in resistance. After a six minutes delay (following cigarette extinguishment), a new burn was begun, followed by two additional ten cigarette exposures. The absence of significant recovery time post-exposure decreased the absolute increase in signal (although the third and fourth exposures provided similar increases) with measured changes in resistance of 110%, 25%, 15% and 9%. The fresh air purge at the end of the experiment did lower the signal substantially. Most importantly, this particular study indicated that the film is sensitive to its environment, even if the ambient atmosphere has a relatively heavy concentration of smoking generated nicotine.

This analysis demonstrated that a simple chemiresistor based on a polyaniline film and interdigitated electrode can monitor nicotine to provide a real time indication of exposure to second hand cigarette smoke. The polyaniline film was shown to be sensitive to the number of cigarettes consumed, demonstrated reasonable recovery between exposures and was functional in the presence of simulated heavy smoking. The detection of nicotine outgassing or "third hand smoke" was also demonstrated to be feasible using the polymer film assembly.

What is claimed is:

1. A device for monitoring exposure to airborne contaminants of tobacco smoke, comprising:
    a conductive polyaniline bulk film molecularly imprinted with an airborne contaminant of tobacco smoke, the conductive polyaniline bulk film having resistance sensitive to binding of the airborne contaminant thereto and being fully protonated prior to said binding; and
    a sensor having interdigitated electrodes, located on a surface of the conductive polyaniline bulk film for passing current through the conductive polyaniline bulk film to measure the resistance only of the conductive polyaniline bulk film.

2. The device of claim 1, wherein the airborne contaminant is nicotine.

3. The device of claim 1, the conductive polyaniline bulk film being formed by at least (a) dissolving conductive polyaniline bulk in a protonating agent to produce a partially protonated, conductive polyaniline bulk solution, (b) depositing the partially protonated, conductive polyaniline bulk solution on a substrate to form the conductive polyaniline bulk film with partial protonation, and (c) doping the conductive polyaniline bulk film with a secondary dopant to fully protonate the conductive polyaniline bulk film.

4. The device of claim 3, the protonating agent being at least 98% pure.

5. The device of claim 4, the protonating agent being formic acid.

6. The device of claim 3, the secondary dopant being HCl.

7. A device for monitoring exposure to an airborne contaminant of tobacco smoke in an air sample, comprising:

a conductive polyaniline bulk film having resistance sensitive to binding of the airborne contaminant of tobacco smoke thereto and being fully protonated prior to said binding; and interdigitated electrodes, located on a surface of the conductive polyaniline bulk film, for passing current through the conductive polyaniline bulk film such that resistance only of the conductive polyaniline bulk film is measurable using the interdigitated electrodes.

8. The device of claim 7, the conductive polyaniline bulk film being molecularly imprinted with the airborne contaminant.

9. The device of claim 7, the airborne contaminant being nicotine.

10. The device of claim 7, the conductive polyaniline bulk film being formed by at least (a) dissolving a conductive polyaniline bulk in a protonating agent to produce a partially protonated, conductive polyaniline bulk solution, (b) depositing the partially protonated, conductive polyaniline bulk solution on a substrate to form the conductive polyaniline bulk film with partial protonation, and (c) doping the conductive polyaniline bulk film with a secondary dopant to fully protonate the conductive polyaniline bulk film.

11. The device of claim 10, the protonating agent being at least 98% pure.

12. The device of claim 11, the protonating agent being formic acid.

13. The device of claim 10, the secondary dopant being HCl.

14. A device for monitoring exposure to an airborne contaminant of tobacco smoke in an air sample, comprising:

a conductive polyaniline bulk film having resistance sensitive to binding of the airborne contaminant of tobacco smoke thereto when being exposed to the air sample; and two interdigitated electrodes, separated apart by approximately 20 microns and located on a surface of the conductive polyaniline bulk film, for passing current through the conductive polyaniline bulk film such that resistance only of the conductive polyaniline bulk film is measurable using the two interdigitated electrodes.

15. The device of claim 14, the conductive polyaniline bulk film having thickness of approximately 100 nanometers.

16. The device of claim 14, the conductive polyaniline bulk film being a conductive bulk polyaniline film.

17. The device of claim 16, the conductive polyaniline bulk film being protonated.

* * * * *